United States Patent [19]
Gerard oosterhuis et al.

[11] Patent Number: 4,935,348
[45] Date of Patent: Jun. 19, 1990

[54] METHOD FOR THE CARRYING OUT OF A MICROBIOLOGICAL OR ENZYMATIC PROCESS

[75] Inventors: Nicholaas M. Gerard oosterhuis, Roosendaal; Kees Koerts, Driebergen, both of Netherlands

[73] Assignee: Cooperatieve Vereniging Suiker Unie U.A., Breda, Netherlands

[21] Appl. No.: 796,919

[22] Filed: Nov. 12, 1985

[30] Foreign Application Priority Data

Nov. 15, 1984 [NL] Netherlands .......................... 8403497
Mar. 4, 1985 [NL] Netherlands .......................... 8500602

[51] Int. Cl.$^5$ .......................... C12P 1/00; C12P 19/04; C17P 19/06; C12Q 3/00
[52] U.S. Cl. .......................................... 435/41; 435/3; 435/111; 435/114; 435/813; 435/818; 435/819
[58] Field of Search ............... 435/289, 819, 101, 313, 435/314, 315, 316, 813, 104, 3, 818, 41

[56] References Cited

U.S. PATENT DOCUMENTS

| | | | |
|---|---|---|---|
| 2,188,192 | 1/1940 | Scholler et al. | 435/315 |
| 3,257,362 | 6/1966 | Norwood | 260/88.2 |
| 3,630,848 | 12/1971 | Lefrançois | 435/813 |
| 3,672,953 | 6/1972 | Coty et al. | 195/28 |
| 3,847,748 | 11/1974 | Gibson et al. | 435/813 |
| 4,025,394 | 5/1977 | Young | 435/315 |
| 4,181,576 | 1/1980 | Malick | 435/813 |

FOREIGN PATENT DOCUMENTS

| | | | |
|---|---|---|---|
| 0017451 | 10/1980 | European Pat. Off. | 435/315 |
| 0111253 | 6/1984 | European Pat. Off. | |
| 2209837 | 7/1974 | France | |
| 2259903 | 8/1975 | France | |
| 54-41381 | 4/1979 | Japan | 436/813 |

Primary Examiner—Christine M. Nucker
Assistant Examiner—William H. Beisner
Attorney, Agent, or Firm—Webb, Burden, Ziesenheim & Webb

[57] ABSTRACT

To improve the yield and/or reduce the energy cost in carrying out a microbiological or enzymatic process in a reactor and to make the reaction conditions essentially independent of the size of the reactor, it is proposed to make use, as a reactor, of an endless circulation tube in which the reaction components are circulated essentially according to a plug flow and in this process are fed through one or more in-line mixers fitted inside the tube. This method and reactor are suitable in particular for the preparation by fermentation of polysaccharides, especially xanthan, in which water, a production medium containing one or more sugars and nutrient salts and an inoculating material of a suitable aerobic bacterium are introduced into the said reactor tube and exposed to fermentation with air being supplied. Preferably the concentration of a reaction component or a value derived therefrom is measured at least one point and the reaction velocity is regulated on the basis of the said measurement within critical limits.

6 Claims, 3 Drawing Sheets

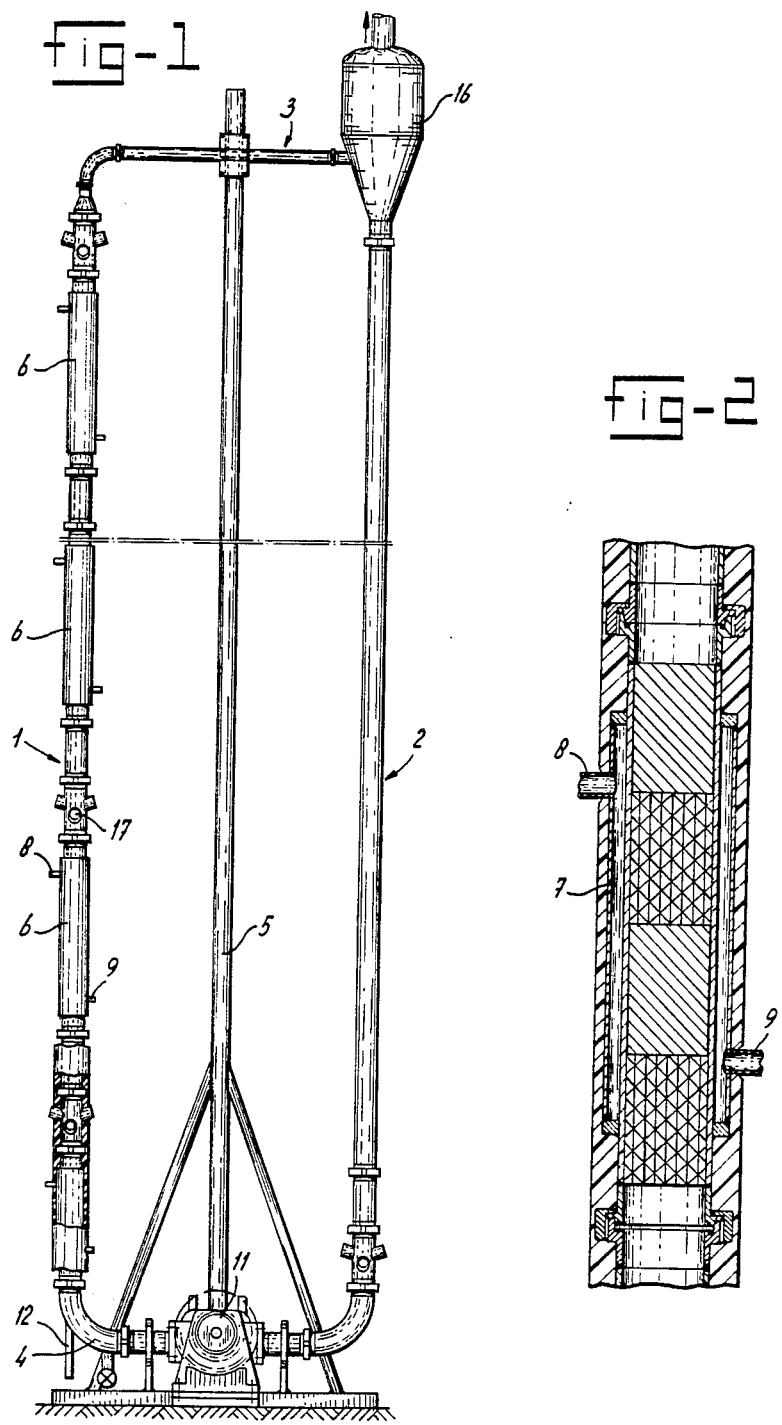

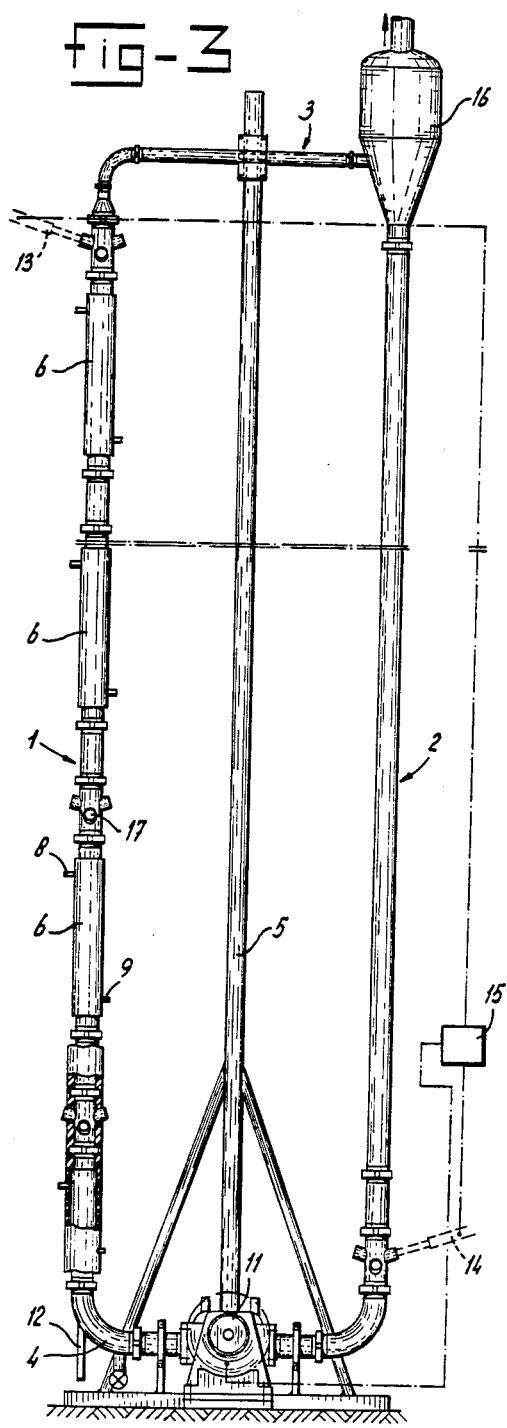

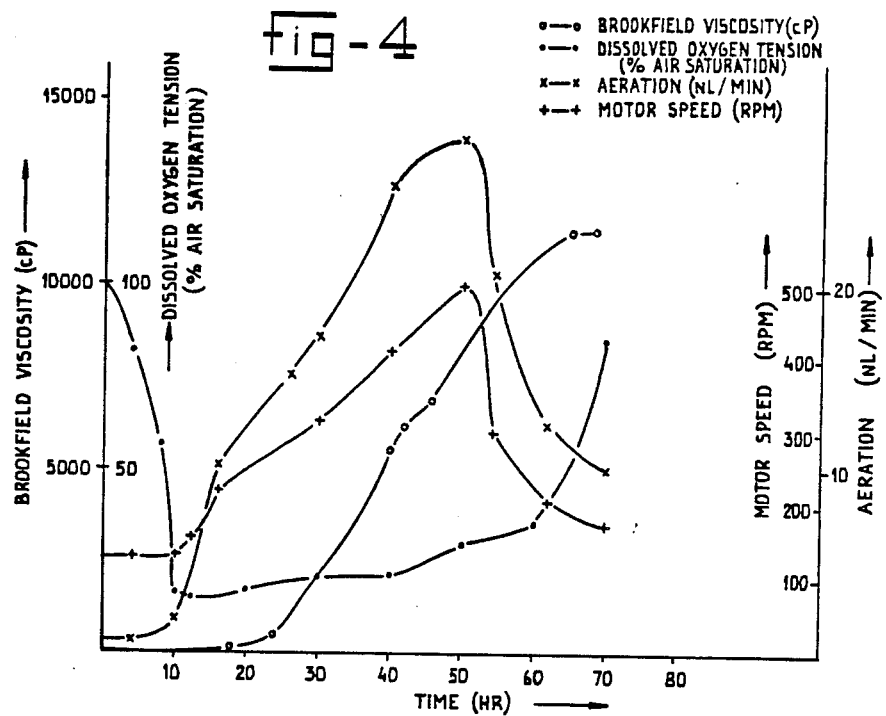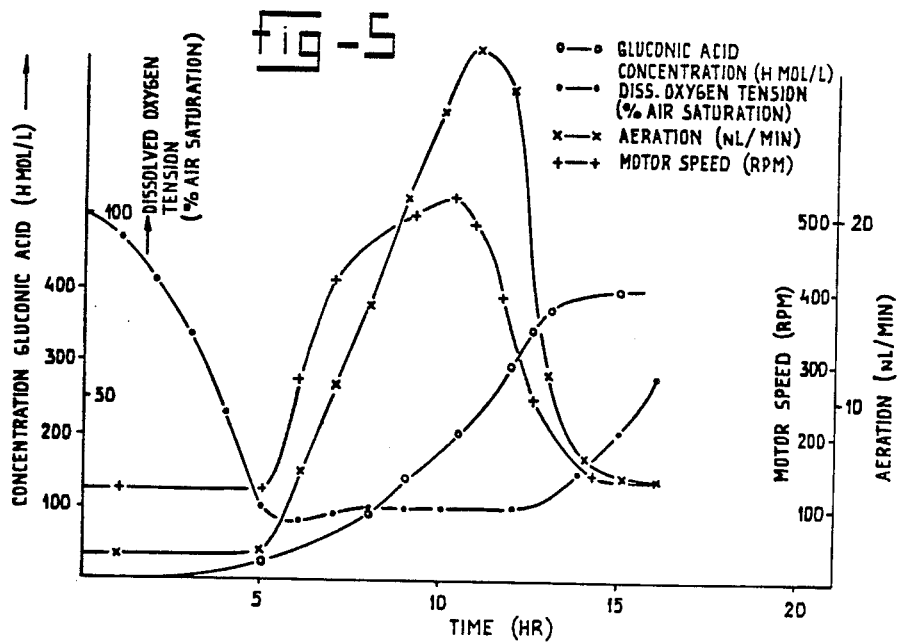

4,935,348

METHOD FOR THE CARRYING OUT OF A MICROBIOLOGICAL OR ENZYMATIC PROCESS

BACKGROUND OF THE INVENTION

The invention relates in the first instance to a method for the carrying out of a microbiological or enzymatic process in which reaction components are fed into a reactor constructed as an endless circulation tube and a circulation current is brought about inside the said tube.

A method of this type is known from the published French Patent Application No. 2,209,837.

It is usual to carry out microbiological or enzymatic processes in a vessel provided with one or more stirring elements (see for example the published European Patent Application No. 0,111,253). It has become evident that when a reactor of this type is used, a considerable spread occurs in the reaction time, i.e. the time that a small element of liquid requires in order to be conveyed around through the vessel starting from the stirrer and to be conveyed back to the stirrer. This spread has an unfavourable influence on the yield of the process since the liquid particles with a relatively rapid circulation time will be subjected too briefly to the treatment (inadequate conversion), whereas liquid particles with a slow circulation time will be exposed too long to the treatment. In certain processes the viscosity increases during the fermentation process and from a certain viscosity value upwards the stirrer generates a revolving cylinder while the remainder remains essentially stationary In the case of aerobic fermentation processes, to promote the multiplication of aerobic bacteria and their product formation, air is supplied to the reaction mixture If a stirred container is used, a relatively high oxygen concentration may occur at the stirrer and a relatively low oxygen concentration at the vessel wall. These disadvantageous phenomena are intensified as the rheological properties of the mixture change. In order, nevertheless, to achieve as complete a reaction as possible, high energy costs are often necessary, the energy being primarily used for the stirring. Another problem of carrying out a process in a stirred container is that enlargement (scaling up) of the equipment from the laboratory scale to the industrial scale is accompanied by a considerable change in the conditions under which the process proceeds.

These drawbacks are not removed by the method according to the said French Patent Application 2,209,837 since there are located inside the tube driven propellers which provide both for the circulation and for the mixing by means of stirring. To this known method there also pertain the disadvantages of high energy costs, relatively low yield and uncontrollable differences in oxygen concentration.

SUMMARY OF THE INVENTION

The object of the invention is to avoid the above named drawbacks and to provide a method referred to in the introduction, in which the reaction conditions on scaling up are essentially independent of the size of the reactor and the energy used is limited to a minimum.

According to the invention the method for this purpose is characterized in that the reaction components are circulated in the completely filled tube by a plug flow and during this process are guided through one or more in-line mixers fitted inside the tube.

The method according to the invention is, in particular, suitable for the preparation by fermentation of polysaccharides, in particular xanthan, production medium containing water, one or more sugars and nutrient salts and an inoculation material of a suitable aerobic bacterium being introduced into the endless reaction tube and the medium in the $said tube being exposed to fermentation with air being supplied.

If a constant circulation rate is used, very handsome results can be achieved which stand out far above the results of a stirred vessel. It is, however, in general advisable to measure the concentration of a reaction component or a value derived therefrom at at least one point and on the basis of the said measurement to regulate the reaction rate within critical minimum and maximum limits in accordance with the kinetics of the process.

It is pointed out that from the published European Patent Application No. 0,111,253 a method is known for the carrying out of a chemical reaction, in particular a biochemical reaction, which method is carried out in a reactor vessel which is divided into two chambers by a wall; the vessel is not entirely filled and no plug flow is brought about. There is also no mention of in-line mixers. The concentration of a reaction component, in particular of the reaction-retarding component, is indeed measured directly or indirectly and on the basis of the said measurement the supply of one or more new components to the reactor is regulated in a manner such that a maximum is not exceeded.

By the reaction rate of an enzymatic or microbiological process is meant the rate at which a certain degree of chemical conversion is reached. This may involve the rate of a certain oxygen absorption, carbonic acid production, heat generation, substrate consumption, product formation and the like. In general it is true that the reaction rate increases up to a certain concentration of a reaction component (C-minimum critical), then remains more or less constant up to a certain higher concentration of the said component (C-maximum critical) and finally decreases at concentrations of the said component which are still higher. It will be clear that it is beneficial that during the carrying out of a process the concentration of a component is held between the critical minimum and maximum concentration values. By using the closed tube which is completely filled with reaction components and in which plug flow is maintained inter alia by means of in-line mixers, the concentration of the component or of several components can be held between the critical values by controlling the reaction rate by means of one or more concentration measurements or measurements of values derived therefrom. In particular, the rate of flow of the plug flow is suitable for being controlled on the basis of the measurement or measurements of the concentration of a component or a value derived therefrom. This rate of flow determines in fact the contact time between the different reaction components, while transport parameters (gas liquid; liquid-liquid; solid-liquid) are also determined by the rate of flow.

Besides opting for the regulation of the rate of flow of the plug flow it is possible to opt for the regulation of the rate of supply of a substrate - this is a reaction component which is used as a nutrient. In the case of aerobic microbiological product formation one of the substrates consists of atmospheric oxygen. The consequence is that the concentration of the substrate in the circulation tube directly behind the mixer will be lower than the critical maximum value, whereas directly before the mixer, i.e at the end of the circulation path, this value must be higher than the critical minimum value. The reaction rate can be controlled by supplying more or less substrate on the basis of measurements of the substrate concentration with a carefully chosen circulation rate of the plug flow. To achieve an energy saving it is, however, preferable, with a carefully chosen substrate supply, to control the reaction rate by regulating the rate of flow of the plug flow on the basis of measurements of the concentration of a reaction component or of a value derived therefrom. Incidentally, the possibility is not excluded that the reaction rate is controlled by the simultaneous regulation of the rate of plug flow and the supply of a reaction component.

This process is influenced, inter alia, also by the number of substrate injection points and the dimensioning of the static mixing elements and the number thereof. For a given device, however, these are usually fixed and are therefore usually unsuitable for subjection to regulation.

It is essential for the effect of the invention that both the optimization of the reactor and the control of the process conditions are determined by the reaction kinetics.

The use of static mixers has the advantage that relatively little energy is used and the reaction volume can be relatively small, while the liquid is conveyed as a plug flow In addition to the preparation by fermentation of polysaccharides from water, glucose and nutrient salts with air as substrate and under the influence of aerobic bacteria, the invention can also be used for the preparation of yeast from water, glucose and nutrient salts and a little yeast. The possibilities also include the preparation of gluconic acid from glucose, the oxidation of ethene by micro-organisms and the preparation of SCP (single cell protein) making use of paraffin dispersed in water.

Instead of the concentration of a reaction component itself a value derived therefrom may be measured, for which, depending on the process, inter alia the pH, the oxygen tension, the temperature and the like are suitable.

The invention also relates to a reactor for the carrying out of microbiological or enzymatic processes consisting of an endless circulation tube with means for the circulation of reaction components fed into the tube. A reactor of this type is known from the already mentioned French Patent Application No. 2,209,837. To be able to carry out the method according to the invention an in-line mixer is fitted in at least one section of the circulation tube, while the reactor is provided with a circulation pump for bringing about a plug flow.

In order to be able to regulate the process between critical minimum and maximum reaction rates, the reactor will have at least one measuring element for the measurement of the concentration of one or more reaction components or a value derived therefrom, while regulating means are present for regulating the pump speed depending on the measured value. Preferably the reactor is provided at at least one point with measuring elements for the measurement of the essentially maximum and the essentially minimum concentration of a reaction component or a value derived therefrom.

A practical embodiment of the reactor embodies a vertical rising tube, a vertical downtube and two horizontal connecting tubes, one or more static mixers being fitted at least in the rising tube, the circulation pump being fitted in the lowermost horizontal tube, a substrate supply element denouncing into the bottom end of the rising tube, a substrate removal element debouching into the top end of the downtube, a measuring element for the measurement of the maximum substrate concentration or a value derived therefrom being fitted in the top end of the rising tube and a measuring element for the measurement of the minimum substrate concentration or a value derived therefrom being fitted in the bottom end of the downtube.

In the preparation of polysaccharides, in particular xanthan, the liquid acquires structural properties, in particular pseudoplasticity, during the fermentation produced by the aerobic bacteria In the case of mixtures which become viscous a pump is always required for the circulation. In the case of the preparation of microbial polysaccharides in which the viscosity remains below a certain value, the circulation can also be brought about by the injection of substrate.

The most important advantage of the invention is that for the same energy consumption the product yield is considerably higher than in the case of a stirred vessel or a closed circulation tube according to the said French Patent Application No. 2,209,837 provided with propeller shaped mixers. If a stirred vessel or the closed tube according to the French application is used, because of the considerable rise in the viscosity it is necessary to stop at a point at which the product yield is still relatively low. This limitation exists to a much lesser extent in the method according to the invention.

BRIEF DESCRIPTION OF THE DRAWINGS

Embodiments of the reactors to be used in the method according to the invention will now be explained in more detail with reference to the figures.

FIG. 1 shows a side view, with a small section in cross-section, of a first embodiment of the reactor according to the invention.

FIG. 2 shows a longitudinal section of a detail.

FIG. 3 shows a side view, with a small section in cross-section, of a second embodiment of the reactor according to the invention.

FIGS. 4 and 5 show two graphs pertaining to Examples 2 and 3 respectively.

DESCRIPTION OF THE PREFERRED EMBODIMENTS

In the two embodiments equivalent components are provided with the same reference numerals.

The reactor shown in FIGS. 1 and 2 consists of an endless circulation tube formed by a rising tube 1, a downtube 2, an uppermost horizontal connecting piece 3 and a lowermost horizontal connecting piece 4. The whole is supported by a stand 5.

The rising tube 1 embodies a number of in-line mixers, preferably constructed as static mixers 6 which are able to mix the reaction components without driven stirring elements by dividing the main currents, interchanging the positions of the partial currents and reuniting the partial currents again. Static mixers are inter alia described in Dutch Patent Application Nos. 75.02953, 77.00090 and 80.04240. Sulzer SMV or SMX mixers are to be preferred. As is evident from FIG. 2, each static mixer is surrounded by a cooling/heating jacket 7 in which a heat transfer medium can be fed or removed through nozzles 8 and 9. Static mixer units may also be fitted in the downtube In the lowermost horizontal section 4 a circulation pump 11 is incorporated, for example constructed as a gear pump.

The reactor operates in general in a batch manner, although continuous supply and removal of reaction components are not excluded. The reactor is first completely filled with the reaction component, i.e. in the case of the preparation of polysaccharides by fermentation, a production medium which contains water, one or more sugars and nutrient salts and an inoculation material of a suitable aerobic bacterium. In the case of xanthan this bacterium is Xanthomonas campestris ATCC 13951. After the filling, the pump 11 is switched on to bring about a plug flow and air is fed in as substrate via the pipe 12. In the static mixers an intimate mixing of the reaction components takes place. The components are partially consumed by the aerobic bacterial as a result of which the bacteria multiply and excrete a product In the preparation by fermentation of polysaccharides atmospheric oxygen is made use of as substrate and the said oxygen is consumed by the aerobic bacteria. After mixing excess gas will have to be separated off, which takes place at the liquid-gas separator 16.

Between the static mixers the reactor may also embody intermediate pieces 17 through which certain components may be supplied.

Important advantages of the reactor constructed as a closed tube in which at least in one part of the tube in-line mixers are fitted and in which a circulation pump provides for the bringing about of a plug flow are that the conditions under which the reaction takes place, independently of the size of the reactor, can be optimised and that the energy consumption can be limited to a minimum. The scaling up of the process is facilitated by the fact that the course of the process in the reactor can be described, and consequently modelled, well. Microbial polysaccharides have the property that they strongly influence the rheology of the medium. In relation to a Stirred vessel an energy saving is always achieved even if the circulation rate is chosen too low and the oxygen is completely consumed before the product has reached the bottom of the downtube. In the preparation of polysaccharides good results can be achieved even with a constant circulation rate.

It is, however, preferable to make use of the reactor according to FIG. 3 in which the concentration of a reaction component of a value derived therefrom is measured at one or more points and the reaction rate is regulated on the basis of the said measurement In FIG. 3 measurement electrodes 13 and 14 are disposed at the top end of the rising tube 1 and at the bottom end of the downtube respectively These measurement electrodes are connected to a regulating unit 15 which controls the pump 11 in a manner such that the reaction rate comes to rest within critical minimum and maximum limits. In particular, the measurement electrode 13 will be used to determine the maximum concentration of substrate after mixing, whereas the purpose of the measurement electrode 14 is to determine the minimum concentration of substrate To achieve an optimum reaction rate, the plug flow rate will be adjusted by the pump in a manner such that the concentration of the substrate always comes to rest within a maximum and minimum critical value. All this implies specifically that if the measurement electrode 13 determines that the maximum concentration of substrate comes to rest above the critical maximum value, the pump speed will be reduced, whereas if the measurement electrode 14 measures that the minimum substrate concentration comes to rest below the critical minimum value, the pump speed will be increased.

The measurement electrodes measure the concentration of the substrate or another reaction component itself or a value which is a direct function of the said concentration, for which, depending on the process, inter alia the pH, oxygen tension, the temperature and the pressure are suitable.

In the embodiment shown in FIG. 3 the pump speed is regulated to allow the reaction to proceed in an optimum manner. The possibility is not excluded that the pump speed is constant and that the supply rate of substrate and/or other reaction components is regulated on the basis of measurements of concentrations or values derived therefrom. Injection can take place at more places and the number of injection points may be varied on the basis of the said measurements. The possibilities also include regulation of the product removal rate.

The reactors described can be used for various microbiological and/or enzymatic processes. They are, in particular, suitable for the production of substances which strongly affect the rheology of the medium (for example, microbial polysaccharides). This is because the flow is well defined and can be kept constant the hydrodynamic conditions by varying the liquid flow rate.

EXAMPLE I

Xanthomonas campestris ATCC 13951 is cultivated at 30° C. on a trypton glucose yeast extract agar for 48 hours. From a loosely disposed colony material is inoculated into a flask containing glucose yeast extract-malt extract solution and suspended, after which cultivation is carried out for 24 hours at 30° C. with shaking. 1 liter of this inoculation material is added to 25 liters of fermentation medium containing glucose as a carbon source in a concentration of 4 % by weight and yeast extract as an organic nitrogen source in a concentration of 0.5 % by weight. Magnesium ions are added as $MgSO_4$ in a concentration of 0.05 % by weight. The pH is kept constant between 6.5 and 7.5 during the fermentation by adding KOH in a concentration of 2N. A basic buffer is used in the form of $K_2HPO_4$ in a concentration of 0.2 % by weight. This material was contained in a reactor tube as described above with a volume of 30 liters. The circulation time was 2 minutes so that the circulation speed was 15 liter/minute. The temperature was 29° C. and 10 liters of air were fed in per minute. The circulation of the material was continued for 72 hours. It emerged that 3 % by weight of xanthan was formed, 4 kW of energy being used per $m^3$ of reactor volume. With the same energy input (4 $kW/m^3$) in a stirred vessel (on a 30 liter scale) the fermentation lasts 144 hours. The product concentration achieved is then also 3 % by weight. On a pilot plant scale this product concentration is achieved in 144 hours with an energy input of 4–5 $kw/m^3$ using a stirred vessel. However, in 72 hours a much lower product concentration, viz. 1.8–2.0 % is obtained with this energy input.

EXAMPLE II

Xanthomonas campestris ATCC 13951 is cultivated at 30° C. on a trypton glucose yeast extract agar for 48 hours. From a loosely disposed colony material is inoculated into a flask containing glucose yeast extract-malt extract solution and suspended, after which cultivation is carried out for 24 hours at 30° C. with shaking. 1 liter of this inoculation material is added to 25 liters of fermentation medium containing glucose as a carbon source in a concentration of 4 % by weight and yeast extract as an organic nitrogen source in a concentration of 0.5 % by weight. Magnesium ions are added as $MgSO_4$ in a concentration of 0.05 % by weight. The pH is kept constant between 6.5 and 7.5 during fermentation by adding KOH in a concentration of 2N. A basic buffer is used in the form of $K_2HPO_4$ in a concentration of 0.2 % by weight. The fermentation is carried out for 65 hours at 30° C. in a reactor tube as described above with a volume of 30 liters. During the fermentation the oxygen tension of the liquid measured by means of an oxygen electrode at point 14 is regulated to a value of approximately 15-25 % of saturation with air. For this purpose, by means of the signal from the said electrode, via suitable transducers, the speed of the pump motor and the quantity of air fed in via the connection at point 12, are regulated.

The course of this fermentation is shown in FIG. 4. This shows in succession, as a function of the time, the viscosity of the fermentation medium (expressed as Brookfield viscosity at 30 rpm measured with an LVT spindle), the oxygen tension in the solution (expressed as a percentage of saturation with air), the speed of the pump motor (expressed in revolutions per minute), and the quantity of air supplied (expressed in normal liters of air per minute)

EXAMPLE III

Gluconobacter oxydans ATCC 621 H is cultivated for 24 hours on a slant agar tube containing a glucose yeast extract-chalk medium. From this tube all the bacteria material is inoculated into a flask of glucose yeast extract-chalk solution and suspended and incubated for 12 hours at 30° C. with shaking. 1 liter of this inoculation material is added to 25 liters of fermentatioan medium containing a glucose (10 % by weight) yeast extract (1 % by weight) medium. During the fermentation the pH is regulated to 3.5 by adding NaOH in a concentration of 4 N. The fermentation is carried out in a reactor tube as described above with a volume of 30 liters for 15 hours at a temperature of 30° C. During the fermentation the oxygen tension of the liquid measured by means of an oxygen electrode at point 14 is regulated to a value of 15-25 % of saturation with air. For this purpose, by means of the signal from the said electrode, via suitable transducers, the speed of the pump motor and the quantity of air supplied via the connection at point 12 are regulated.

The course of this fermentation is shown in FIG. 5. This shows in succession, as a function of time, the concentration of gluconate in the fermentation medium (expressed in mol of gluconic acid/liter), the oxygen tension in the solution (expressed as a percentage of saturation with air), the speed of the pump motor (expressed in revolutions per minute) and the quantity of air supplied (expressed in normal liters of air per minute).

We claim:

1. Method for the carrying out of a microbiological or enzymatic process comprising: feeding a quantity of reaction components into a circulation tube reactor in an amount sufficient to fill said circulation tube completely, bringing about a circulation current inside said circulation tube reactor by a pump, mixing said components by static in-line mixers inside said circulation tube reactor, and separating gas and liquid from each other, wherein said circulation tube reactor is a vertical tube loop having a substantially vertical rising tube in which the mixture flows upwards as a plug flow, said vertical tube loop further having a substantially vertical downtube in which the mixture flows downwards and two relatively short connecting tubes connecting said rising tube and said downtube at their upper and lower ends, further wherein the mixing of said components by said static in-line mixers takes place in said rising tube, and further wherein a substrate gas is introduced in the lower part of said rising tube and the separation of gas and liquid take place in the uppermost part of said vertical tube loop.

2. Method according to claim 1, wherein said step of feeding a quantity of reaction components into a circulation tube further comprises feeding a production medium containing water, one or more sugars and nutrient salts and an inoculation material of a suitable aerobic bacterium into said circulation tube reactor, and wherein the production medium is then supplied with air.

3. Method according to claim 1 or 2, wherein at at least one point the concentration of a reaction component or a value derived therefrom is measured and on the basis of said measurement the reaction rate is regulated within critical minimum and maximum limits in accordance with the kinetics of the process.

4. Method according to claim 3, wherein the reaction rate is regulated by means of the regulation of the flow rate of the plug flow in the circulation tube.

5. Method according to claim 3, wherein the reaction rate is regulated by means of the regulation of the supply of reaction components of the circulation tube.

6. Method according to claim 3, wherein xanthan is prepared in said production medium.

* * * * *

UNITED STATES PATENT AND TRADEMARK OFFICE
CERTIFICATE OF CORRECTION

PATENT NO. : 4,935,348

DATED : June 19, 1990

INVENTOR(S) : Nicolaas Marius Gerard Oosterhuis and Kees Koerts

It is certified that error appears in the above-identified patent and that said Letters Patent is hereby corrected as shown below:

On the title page, under item [19], "Gerard oosterhuis et al." should be --Oosterhuis--; and in item [75], "Nicholaas M. Gerard oosterhuis" should be --Nicholaas M. G. Oosterhuis--.

Column 1 Line 30 after "stationary" insert --.--.

Column 1 Line 33 after "mixture" insert --.--.

Column 2 Line 5 "$aid" should read --said--.

Column 3 Line 27 after "flow" insert --.--.

Column 4 Line 1 "denouncing" should read --debouching--.

Column 5 Line 18 after "product" insert --.--.

Column 5 Line 39 "Stirred" should read --stirred--.

Column 5 Line 47 "of" should read --or--.

UNITED STATES PATENT AND TRADEMARK OFFICE
CERTIFICATE OF CORRECTION

PATENT NO. : 4,935,348

DATED : June 19, 1990

INVENTOR(S) : Nicolaas Marius Gerard Oosterhuis and Kees Koerts

It is certified that error appears in the above-identified patent and that said Letters Patent is hereby corrected as shown below:

Column 5 Line 52 after "respectfully" insert --.--.

Column 5 Line 60 after "substrate" insert --.--.

Column 7 Line 28 after "minute)" insert --.--

Column 7 Line 41 "4 N" should read --4N--.

Column 8 Line 2 "mol" should read --mmol--.

Signed and Sealed this

Twenty-third Day of July, 1991

Attest:

HARRY F. MANBECK, JR.

*Attesting Officer*  *Commissioner of Patents and Trademarks*